United States Patent
Fischer et al.

(10) Patent No.: US 6,350,924 B1
(45) Date of Patent: Feb. 26, 2002

(54) METHOD FOR PRODUCING 1,4-BUTANEDIOL

(75) Inventors: Rolf Fischer, Heidelberg; Gerd Kaibel, Lampertheim; Rolf Pinkos, Bad Dürkheim; Ralf-Thomas Rahn, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/673,134

(22) PCT Filed: Apr. 16, 1999

(86) PCT No.: PCT/EP99/02587

§ 371 Date: Oct. 11, 2000

§ 102(e) Date: Oct. 11, 2000

(87) PCT Pub. No.: WO99/55659

PCT Pub. Date: Nov. 4, 1999

(30) Foreign Application Priority Data

Apr. 23, 1998 (DE) .................................. 198 18 248

(51) Int. Cl.$^7$ .......................... C07C 27/00; C07C 31/18
(52) U.S. Cl. ..................... 568/864; 568/852; 568/861
(58) Field of Search ............................. 568/852, 861, 568/864

(56) References Cited

U.S. PATENT DOCUMENTS 6,100,410 A * 8/2000 Tuck et al. ................. 549/325

FOREIGN PATENT DOCUMENTS

| DE | 25 43 673 | 4/1976 |
|----|-----------|--------|
| DE | 25 53 959 | 6/1976 |
| GB | 1 454 440 | 11/1976 |
| GB | 1 464 263 | 2/1977 |
| WO | 97/43242 | 11/1997 |
| WO | WO-9743242 A * | 11/1997 |

* cited by examiner

Primary Examiner—Johann Richter
Assistant Examiner—Elvis O. Price
(74) Attorney, Agent, or Firm—Keil & Weinkauf

(57) ABSTRACT

A process for preparing 1,4-butanediol and, if desired, γ-butyrolactone and THF by oxidizing butane or benzene to form a product stream including maleic anhydride, absorbing maleic anhydride from the product stream with a high-boiling inert solvent in an absorption stage to give a liquid absorption product, esterifying the liquid absorption product with a $C_1$–$C_5$ esterifying alcohol in an esterification stage to form an esterification product comprising the corresponding diester and high-boiling inert solvent, then hydrogenating the esterification product to give a hydrogenation product which comprises the products of value, 1,4-butanediol and, if desired, γ-butyrolactone and tetrahydrofuran and the esterifying alcohol and which is separated by distillation into the products of value and the esterifying alcohol, and recycling the esterifying alcohol to the esterification zone, which comprises separating the esterification product into the diester and the inert solvent by distillation under reduced pressure prior to the hydrogenation, recycling the inert solvent to the absorption stage, and hydrogenating the diester in the liquid phase over a fixed-bed catalyst.

10 Claims, No Drawings

METHOD FOR PRODUCING 1,4-BUTANEDIOL

This is the National Phase application of PCT/EP99/02587, filed Apr. 16, 1999.

The invention relates to a process for preparing 1,4-butanediol plus if desired tetrahydrofuran (THF) and γ-butyrolactone (GBL) from waste gases from the oxidation of butane and/or benzene by absorbing maleic anhydride (MA) with high-boiling solvents, esterifying the maleic anhydride with an alcohol to form the diester, and catalytically hydrogenating the maleic diester.

1,4-Butanediol is an important starting material in preparing polyesters, such as polybutylene terephthalate, and also γ-butyrolactone and THF. Therefore, there are a large number of known processes for preparing 1,4-butanediol and mixtures comprising it from MA obtained by catalytic oxidation of hydrocarbons.

MA, for instance, can be prepared by gas phase oxidation of benzene or n-butane. Along with the MA the gaseous oxidation product generally includes water, oxygen, nitrogen, carbon dioxide, unreacted benzene or butane, and small amounts of formic, acetic, acrylic and propionic acids. These are accompanied by oxidation products of the impurities in the oxidation substrates, such as isobutane. Examples of these products are citraconic anhydride, furan, acrolein, crotonaldehyde, crotonic acid and methacrolein.

Since industry generally requires 1,4-butanediol with purities of more than 99.9%, it has to date been common to achieve this by purifying the MA before subjecting it, for example, to hydrogenation in ester form to give 1,4-butanediol.

WO 97/43242 describes a process for preparing 1,4-butanediol, γ-butyrolactone and THF without pre-purifying the maleic anhydride, which is obtained by catalytic oxidation from benzene, mixed $C_4$-olefinic compounds or n-butane.

In this process there is an absorption zone in which MA from an MA-comprising vapor stream is brought into contact with an organic solvent whose boiling point is at least 30° C. higher than that of the maleic diester. A waste gas stream is retained, and the MA in the high-boiling solvent is reacted with an appropriate $C_1$–$C_4$ alcohol under esterifying conditions in an esterification zone to form the diester. The resultant diester is stripped from the organic solvent with a stream of hydrogen and is hydrogenated in the gas phase over a heterogeneous hydrogenation catalyst. The products of value, 1,4-butanediol, γ-butyrolactone and THF, can be recovered from the hydrogenation product.

This process entails certain disadvantages. When the maleic diester is stripped from the high-boiling solvent it is accompanied by relatively low-boiling compounds originating from impurities in the maleic anhydride, and by solvent traces. These components pass into the hydrogenation phase, with the consequence that the separation method required following hydrogenation is higher.

Furthermore, stripping must be carried out at the same pressure as the gas phase hydrogenation. This requires the circulation of a considerable stream of hydrogen (in the example of WO 97/43242, 320 mol of hydrogen to each mole of diester). The high stripping temperatures which occur may cause cracking processes to take place.

Further disadvantages arise in the gas phase hydrogenation. For instance, the temperature of the gas stream must be kept above the dew point of the maleic diester. This requires a considerable hydrogen stream, and the recycling of the excess hydrogen entails high energy costs. The short residence time during the gas phase hydrogenation leads to the formation of by-products and thus to a reduction in yield and an increase in the separation method at the distillation stage. The catalyst loadings (space velocities) possible in the gas phase hydrogenation of maleic diesters are low: otherwise, the adiabatic temperature increase over the reactor becomes too great and leads to a reduction in selectivity. Countering this by raising the amount of hydrogen, although possible, is uneconomic owing to the high costs of circulated gas.

It is an object of the present invention to provide a process for preparing 1,4-butanediol and, if desired, γ-butyrolactone and THF which produces 1,4-butanediol in a good yield and high purity without the need to purify the maleic anhydride beforehand and which is simple and cost-effective.

We have found that this object is achieved by a process for preparing 1,4-butanediol and, if desired, γ-butyrolactone and THF by oxidizing n-butane or benzene to form a product stream including maleic anhydride, absorbing maleic anhydride from the product stream with a high-boiling inert solvent in an absorption stage to give a liquid absorption product, esterifying the liquid absorption product with a $C_1$–$C_5$ esterifying alcohol in an esterification stage to form an esterification product comprising the corresponding diester and high-boiling inert solvent, then hydrogenating the esterification product to give a hydrogenation product which comprises the products of value, 1,4-butanediol and, if desired, γ-butyrolactone and THF and which is separated by distillation into the products of value and the esterifying alcohol, and recycling the esterifying alcohol to the esterification zone. The process of the invention then comprises separating the esterification product into the diester and the inert solvent by distillation under reduced pressure prior to the hydrogenation, recycling the inert solvent to the absorption stage, and hydrogenating the diester in the liquid phase over a fixed-bed catalyst.

This process enables the obtention from maleic anhydride of the products of value, of 1,4-butanediol and, if desired, γ-butyrolactone and THF, in cost-effective manner and in good yield in a few simple steps. Because of the distillative purification of the esterification product prior to hydrogenation, the products of value can be obtained in high purity following the hydrogenation. Liquid rather than gas phase hydrogenation allows high catalyst loadings, further increasing the economy of the process of the invention.

Following the distillation of the hydrogenation product it is possible by virtue of the process of the invention to obtain 1,4-butanediol in a purity of more than 99.9 mol %, preferably at least 99.95 mol %.

The highly pure 1,4-butanediol recovered is outstandingly useful as a starting material for preparing polyesters such as polybutylene terephthalate and for preparing γ-butyrolactone and THF.

The preparation of the maleic anhydride takes place by oxidizing benzene or n-butane, generally in the gas phase over a vanadium oxide based catalyst. The process can be carried out exactly as described in WO 97/43242, or similarly. The partial oxidation of benzene is customarily performed using a supported vanadium pentoxide catalyst which is activated, for example, with $MoO_3$. The reaction temperature is from 400 to 455° C. and the reaction pressure from about 1 bar to about 3 bar. The amount of air used is about four times that dictated by theory, so as not to exceed the explosion limits. The contact time is approximately 0.1 second.

If n-butane is used as starting material, it is common to use vanadium pentoxide as catalyst at a temperature from about 350 to about 450° C. and a pressure from about 1 bar to about 3 bar. If a suitable reactor is used the ratio of air to n-butanol can be about 20:1, despite the fact that per se this ratio leads to a mixture which is easily ignited.

The result is a gaseous oxidation product which generally comprises not only maleic anhydride but also water, oxygen, nitrogen, carbon dioxide, unreacted benzene or n-butane and fairly small amounts of organic impurities such as formic, acetic, acrylic and propionic acids. There may also be oxidation products of impurities from the starting materials in the oxidation product.

The absorption of the maleic anhydride contained in the gaseous oxidation product from the oxidation of benzene or n-butane can take place in an absorption stage in exactly the manner described in WO 97/43242, or similarly, using a high-boiling inert organic solvent. For this purpose the MA-comprising gaseous oxidation product is brought into contact with a high-boiling solvent at a temperature from about 60 to 160° C. and a pressure from about 1 bar to 3 bar to give a liquid absorption product comprising maleic anhydride in the high-boiling solvent.

Absorption of maleic anhydride by the high-boiling organic solvent can be effected by blowing a gaseous stream containing maleic anhydride through the solvent. Alternatively, the solvent can be sprayed into the vapor containing maleic anhydride, or the absorption can be conducted by a countercurrent technique.

Solvents employed with preference are those whose boiling points are at least 10° C. above that of the maleic diester corresponding to the esterifying alcohol. The solvent should be inert toward maleic anhydride and the corresponding diester under the prevailing reaction conditions and should be substantially insoluble in and/or immiscible with water. Examples of suitable high-boiling organic solvents are listed in WO 97/43242.

Examples of suitable solvents are dibutyl phthalate, tricresyl phosphate, dibutyl maleate, waxes of high molecular mass, and aromatic solvents with a molecular weight of between 150 and 400 and a boiling point of more than 140° C., such as dibenzylbenzene and dialkyl phthalate esters. If esters are used it is preferred for the alkyl unit of these esters to correspond to that of the esterifying alcohol, so as to avoid instances of transesterification. If methanol was used as the esterifying alcohol, therefore, it is preferred for the high-boiling ester used to be, for example, dimethyl phthalate, dimethyl 2,3-naphthalenedicarboxylate, dimethyl cyclohexanedicarboxylate, or methyl esters of long-chain fatty acids. It is also possible to employ high-boiling ethers, such as tetraethylene glycol dimethyl ether.

The absorption product comprising maleic anhydride and the high-boiling inert solvent is reacted in an esterification stage with a $C_1$–$C_5$ monoalcohol to esterify the maleic anhydride and so form maleic diesters, in a manner exactly the same as or similar to that described in WO 97/43242. In general, esterifying alcohols employed comprise methanol, ethanol, n-propanol, n-butanol, isobutanol, n-pentanol or isopentanol. Methanol and ethanol are preferred. The esterification of the maleic anhydride with alcohol can take place in one or more stages with or without catalyst in the high-boiling solvent.

When using high-boiling alcohols, the noncatalytic reaction can take place at elevated temperature with continuous removal of the water of reaction.

The catalytic esterification of maleic anhydride can be carried out with solid acidic catalysts. An alternative is to employ homogeneously soluble catalysts, such as sulfuric acid, phosphoric acid, p-toluenesulfonic acid, heteropolyacids, or Lewis acids such as tin oleate or tetraalkoxytitanate.

The esterification temperatures are dependent on the alcohol employed, and the esterification is carried out under the autogenous pressure.

Such catalysts can be recycled to the absorption stage together with the organic solvent, provided the solvent boils at a higher level than the maleic diester, and are active again in the subsequent esterification stage.

Separation of the excess alcohol and water of reaction, and of the water entering the esterification stage from the absorption stage, can be carried out during or after the esterification. Before the alcohol is recycled to the esterification stage it is freed from the water, which is removed.

The esterification product obtained is separated by distillation under reduced pressure into the diester and the high-boiling solvent.

The distillation is conducted at a pressure of in general from 30 to 800 mbar, preferably from 50 to 200 mbar, in a distillation column. The liquid-phase temperature is generally from 100 to 250° C., preferably from 120 to 190° C. and, with particular preference, from 125 to 180° C.

In one preferred column setup, for use when the solvent has a boiling point higher than that of the diester, the feed port for the mixture that is to be distilled is located above the liquid phase of the distillation column. The low boilers, such as residual water and the esterifying alcohol, together with the diester, are distilled off at the top of the column. The high-boiling organic solvent together if appropriate with the esterifying catalyst accumulates in the liquid phase of the column.

It is even more advantageous to recover the diester without other low boilers such as residual water and esterifying alcohol. To do this, the diester is withdrawn via a side arm in the rectifying section of the column.

The diester obtained in this way is hydrogenated in the liquid phase over a heterogeneous hydrogenation catalyst at elevated temperature and elevated pressure. Hydrogenation takes place in a single reactor or in a plurality of reactors connected one after the other.

The hydrogenation temperature is generally from 60 to 300° C., preferably from 70 to 250° C. and, with particular preference, from 80 to 240° C. At low temperatures there is preferential hydrogenation of the C—C double bond, at higher temperatures of the ester linkage.

The hydrogenation is conducted under a pressure of generally from 30 to 330 bar, preferably from 50 to 300 bar and, with particular preference, from 100 to 290 bar over a residence time of from 0.5 to 2 hours. The C—C double bond can be hydrogenated at just a low pressure, possibly in a separate stage.

The weight-hourly space velocity (loading) of the hydrogenation catalyst is generally from 0.2 to 1.3 kg of diester/liter of catalyst volume·h, preferably from 0.3 to 1 kg and, with particular preference from 0.35 to 0.8 kg.

In order to dissipate the heat of hydrogenation the hydrogenation of high-energy starting materials in the liquid phase is usually conducted with product recycling, at least in the main reactor. In this case the weight ratio between the circulation (recycled product) and the infeed is generally between 1 and 100, preferably between 2 and 50 and, with particular preference, between 3 and 25.

The molar ratio of fresh hydrogen to diester lies in general between 5 and 8, preferably between 5.01 and 7 and, with particular preference, between 5.02 and 6.

The hydrogenation catalysts employed are generally heterogeneous catalysts suitable for the hydrogenation of carbonyl groups. However unsupported catalysts, catalytically active metals without a carrier material, or supported catalysts, catalysts which include a carrier material, can be used. Supported catalysts are employed with preference.

Examples of suitable hydrogenation catalysts are described in Houben-Weyl, Methoden der organischen Chemie, volume IV/Ic, pp. 16 to 26, Georg Thieme Verlag, 1980.

The hydrogenation catalysts employed in the process of the invention are preferably those whose catalytically active component comprises one or more elements from groups Ib, VIb, VIIb, VIIIb and IIIa, IVa, Va of the Periodic Table of the Elements. Among these, preference is given to the use of copper, chromium, rhenium, cobalt, rhodium, nickel, palladium, iron, platinum, indium, tin and antimony. Particular preference is given to copper, cobalt, palladium, platinum and rhodium, and very particular preference to copper.

Examples of suitable unsupported catalysts are Raney catalysts based on nickel, copper or cobalt; palladium black, platinum black (as they are defined in Houben-Weyl), copper sponge, and alloys or mixtures of, for example, palladium/rhenium, platinum/rhenium, palladium/nickel, palladium/cobalt, palladium/rhenium/silver.

Precipitated catalysts can also be used in the process of the invention. The precipitated catalysts are prepared by precipitating the catalytically active component from solutions of its salt, especially from solutions of the nitrates and/or acetates, by adding, for example, solutions of alkali metal and/or alkaline earth metal hydroxide and/or alkaline earth metal carbonate. For instance, the catalytically active components can be precipitated as, for example, sparingly soluble hydroxides, oxide hydrates, basic salts or carbonates. The precipitates are subsequently dried and calcined at generally from 300 to 700° C., preferably from 400 to 600° C., to convert them to the corresponding oxides, mixed oxides and/or mixed-valence oxides.

The calcined oxidic compounds are reduced by treatment with hydrogen or hydrogen-containing gases to form the corresponding metals and/or oxidic compounds in lower oxidation states, generally at from 50 to 700° C., preferably at from 100 to 400° C., and in this way are converted into the actual catalytically active form. Reduction is continued until water is no longer formed.

The precipitated catalysts may include carrier material. In this case the catalytically active component is precipitated in the presence of the carrier material concerned. In one preferred technique the catalytically active component and the carrier material are precipitated simultaneously from the corresponding salt solutions.

Suitable supported catalysts other than the above-mentioned precipitated catalyst which can be employed as supported catalysts are those where the catalytically active components have been applied to the carrier material by other means.

For example, the catalytically active components can be applied to the carrier material by impregnating it with solutions or suspensions of the salts or oxides of the corresponding elements, drying them and then reducing the metal compounds to the corresponding metals or compounds in a lower oxidation state. The reducing agents are preferably hydrogen or complex hydrides.

The catalytically active component can also be applied to the carrier by impregnating it with solutions of salts which readily undergo thermal decomposition and heating the impregnated carrier at temperatures from 300 to 600° C., whereupon the adsorbed metal compounds undergo thermal decomposition.

Examples of salts which readily undergo thermal decomposition are nitrates and complexes, such as carbonyl complexes or hydrido complexes of the catalytically active metals.

The thermal decomposition is preferably carried out under an inert gas atmosphere. Examples of suitable inert gases are nitrogen, carbon dioxide, hydrogen and noble gases.

Furthermore, the catalytically active component can be applied to the carrier material by vapor deposition or flame spraying.

Alternatively, the catalytically active component can be applied to the carrier by the techniques described in DE-A 25 19 817, EP-A 0 147 219 and EP-A 0 285 420. In the catalysts described in these patents the catalytically active components are in the form of an alloy produced by impregnating the carrier with a salt or complex of the metals concerned and then subjecting the impregnated carrier to heat treatment and/or reduction.

It is also possible for two or more catalytically active metals to be applied as catalytically active components to the respective carrier material.

Carrier materials which can be used are, generally, the oxides of aluminum and of titanium, zirconium oxide, silica, clay earths, such as montmorillonites, silicates such as magnesium or aluminum silicates, zeolites such as ZSM-5 or ZSM-10 zeolites, and activated carbon. It is also possible for mixtures of different carrier materials to serve as carriers for the catalysts employed in the process of the invention.

The amount of catalytically active components present in the supported catalysts is not critical to the success of the process of the invention. To the skilled worker it is obvious that higher proportions of catalytically active components in the supported catalysts may lead to higher space-time conversions than smaller amounts. In general, the amount of catalytically active component in the supported catalyst is from 0.1 to 90% by weight, preferably from 0.5 to 40% by weight, based on the overall mass of the catalyst. These figures relate to the catalyst as a whole including the carrier material. The latter may have different specific densities and specific surface areas, so that amounts above or below these ranges may also be present without having any adverse impact on the result of the process of the invention.

Precipitated and supported catalysts can be activated in situ at the beginning of the reaction by the hydrogen that is present; preferably, however, these catalysts are activated separately before being used.

Examples that may be mentioned of heterogeneous catalysts employable in the process of the invention are as follows: cobalt on activated carbon, cobalt on silica, rhenium on alumina, rhenium on activated carbon, cobalt on alumina, rhenium on activated carbon, rhenium on silica, rhenium/tin on activated carbon, rhenium/platinum on activated carbon, copper on activated carbon, copper chromide, barium copper chromide, copper/aluminum/manganese oxide, copper/alumina/zinc oxide, and also catalysts in accordance with DE-A 39 32 332, US-A 3,449,445, EP-A 0 044 444, EP-A 0 147 219, DE-A 39 04 083, DE-A 23 21 101, EP-A 0 415 202, DE-A 23 66 264 and EP-A 0 100 406. Particular preference is given to the catalysts described in EP-A 0 552 463.

The amount of the products of value, 1,4-butanediol, γ-butyrolactone and THF, in the hydrogenation product may vary. It is determined predominantly by the parameters of pressure, temperature and residence time and by the choice of hydrogenation catalyst.

The amount of γ-butyrolactone can be reduced almost to zero if hydrogenation is conducted at high pressure and low temperature and with a long residence time. The THF content is high if the hydrogenation catalyst has acidic centers.

The molar proportion of the products of value to one another can be, for example, from 70 to 99 mol % 1,4-butanediol, from 0.5 to 29 mol % THF and from 0.1 to 20 mol % γ-butyrolactone, the sum of the fractions of all three products being 100 mol %.

The hydrogenation product is usually separated by distillation. Any of the esterifying alcohol present in the hydrogenation product and liberated in the course of the esterification, in so far as it has not been separated off following the esterification, is first separated from the 1,4-butanediol together with any low boilers present, such as THF. If the amount of THF is sufficiently large to make its isolation worthwhile, the THF is separated off conventionally from the esterifying alcohol before the latter is recycled to the esterification stage.

The product stream comprising 1,4-butanediol is worked up in a manner familiar to the skilled worker and in the course of which it is possible to recover γ-butyrolactone. If there is no desire to recover γ-butyrolactone, it can simply be recycled to the hydrogenation.

Any components present in the hydrogenation product that have not been fully hydrogenated and are high-boiling relative to 1,4-butanediol, such as esters of butanediol and hydroxybutyric acid or succinic acid, can simply be recycled to the hydrogenation. With a gas phase hydrogenation this option will be closed owing to the extremely low volatilities.

The process of the invention enables high-purity 1,4-butanediol with a purity of more than 99.9 mol %, preferably more than 99.95 mol %, to be obtained in a high yield in an economic process.

The examples which follow constitute an additional description of the invention, especially liquid-phase hydrogenation as compared with gas phase hydrogenation.

EXAMPLE 1

In a reactor cascade comprising a main reactor (2.5 l copper catalyst, T 4489, Süd-Chemie AG, Munich, reactor operated with liquid circuit for heat dissipation) and secondary reactor (0.5 l copper catalyst, T 4489) 1.5 kg/h dimethyl maleate (prepared from maleic anhydride on the basis of n-butane by catalytic esterification with methanol and subsequent distillation) are hydrogenated in downflow operation at 250 bar in the liquid phase (weight-hourly space velocity 0.5 kg of diester/liter·h). In the main reactor the entry temperature was 150° C. and the exit temperature 208° C. The secondary reactor was operated at approximately 195° C. The conversion of dimethyl maleate was complete. The yield of 1,4-butanediol was 98 mol % (tetrahydrofuran 1 mol %, γ-butyrolactone 0.4 mol %). 0.5 mol % of n-butanol was formed as a byproduct. The remaining 0.1 mol % was spread between products such as n-propanol, 2-(4-hydroxybutoxy)tetrahydrofuran, 2-methoxytetrahydrofuran and xylene. Fractional distillation (30 mbar) of the reaction product gave butanediol with purities of more than 99.95 GC area %. The reaction products were analyzed by gas chromatography with an internal standard using a flame ionization detector (FID).

COMPARATIVE EXAMPLE

In a tube reactor with 800 ml of copper catalyst T 4489, dimethyl maleate (same quality as in the example according to the invention) was hydrogenated in the gas phase under conditions like those in WO 97/43242 (62 bar, approximately 190° C., weight-hourly space velocity 0.15 kg of diester/liter·h). The yields of the products of value are distributed as follows: 1,4-butanediol 79.1 mol %, γ-butyrolactone 10.4 mol %, tetrahydrofuran 5.3 mol %. The principal byproduct was n-butanol and 4.5 mol %. The remaining 0.7 mol % was spread over products such as n-propanol, 4-hydroxybutyraldehyde, 2-(4-hydroxybutoxy) tetrahydrofuran, 2-methoxytetrahydrofuran, xylene, 1-methoxy-1,4-butanediol, butanediol diethers, methyl 4-hydroxybutyrate and butanediol 4-hydroxybutyrate. Fractional distillation of the hydrogenation product gave maximum butanediol purities of only 98.1 GC area %. The principal concomitant component was γ-butyrolactone at 1 GC area %. Since butyrolactone was present in all of the fractions, there must have been continual formation of a subsequent liquid phase, probably comprising butanediol 4-hydroxybutyrate. The reaction products were analyzed by gas chromatography with an internal standard, using a FID.

We claim:

1. A process for preparing 1,4-butanediol and, if desired, γ-butyrolactone and THF by oxidizing n-butane or benzene to form a product stream including maleic anhydride, absorbing maleic anhydride from the product stream with a high-boiling inert solvent in an absorption stage to give a liquid absorption product, esterifying the liquid absorption product with a $C_1$–$C_5$ esterifying alcohol in an esterification stage to form an esterification product comprising the corresponding diester and high-boiling inert solvent, then hydrogenating the esterification product to give a hydrogenation product which comprises the products of value, 1,4-butanediol and, if desired, γ-butyrolactone and tetrahydrofuran and the esterifying alcohol and which is separated by distillation into the products of value and the esterifying alcohol, and recycling the esterifying alcohol to the esterification zone, which comprises separating the esterification product into the diester and the inert solvent by distillation under reduced pressure prior to the hydrogenation, recycling the inert solvent to the absorption stage, and hydrogenating the diester in the liquid phase over a fixed-bed catalyst.

2. A process as claimed in claim 1, wherein following distillation of the hydrogenation product 1,4-butanediol is obtained in a purity of more than 99.9 mol %.

3. A process as claimed in claim 1, wherein the inert solvent used for absorption has a boiling point higher by at least 10° C. than that of the maleic diester.

4. A process as claimed in claim 1, wherein the esterifying alcohol is a monoalcohol from the group consisting of methanol and ethanol.

5. A process as claimed in claim 1, wherein a homogeneously soluble catalyst is employed as esterification catalyst in the esterification stage.

6. A process as claimed in claim 1, wherein distillation of the esterification product is carried out in a distillation column at a pressure of from 30 to 800 mbar and a liquid-phase temperature of from 100 to 250° C.

7. A process as claimed in claim 1, wherein hydrogenation is carried out at a temperature from 60 to 300° C. and at a pressure of from 30 to 330 bar.

8. A process as claimed in claim 1, wherein the weight-hourly space velocity of the hydrogenation catalyst is from 0.2 to 1.3 kg of diester/liter of catalyst volume·h.

9. A process as claimed in claim 1, wherein the hydrogenation catalyst comprises at least one element from groups Ib, VIb, VIIb, VIIIb, IIIa, IVa and Va of the Periodic Table of the Elements.

10. A process as claimed in claim 1, wherein the molar proportion of the products of value in the hydrogenation product is from 70 to 99 mol % 1,4-butanediol, from 0.5 to 29 mol % THF and from 0.1 to 20 mol % γ-butyrolactone, the sum of the molar fractions of 1,4-butanediol, THF and γ-butyrolactone being 100 mol %.

* * * * *